United States Patent [19]
Bombardelli et al.

[11] Patent Number: 5,273,747
[45] Date of Patent: Dec. 28, 1993

[54] COMMIPHORA MUKUL EXTRACTS AND THERAPEUTICAL APPLICATIONS THEREOF

[75] Inventors: Ezio Bombardelli; Michele Spelta, both of Milan, Italy

[73] Assignee: Indena S.P.A., Milan, Italy

[21] Appl. No.: 882,840

[22] Filed: May 14, 1992

[30] Foreign Application Priority Data

May 15, 1991 [IT] Italy .................... MI91 A 001336

[51] Int. Cl.$^5$ .................... A61K 35/78; A61K 31/58
[52] U.S. Cl. .................... 424/195.1; 514/169; 514/885; 514/886; 514/887
[58] Field of Search .................... 424/195.1; 514/169, 514/886, 887, 885

[56] References Cited

U.S. PATENT DOCUMENTS

| | | | |
|---|---|---|---|
| 4,117,120 | 9/1978 | Elderbaum | 424/195.1 |
| 4,592,912 | 6/1986 | Nickolaus | 424/195.1 |
| 4,713,242 | 12/1987 | Trenzeluk | 424/195.1 |
| 4,719,111 | 1/1988 | Wilson | 424/195.1 |

OTHER PUBLICATIONS

Remington, J. "The Practice of Pharmacy" 3rd ed. J. B. Lippincott, Co. p. 912, 1895.

*Primary Examiner*—John W. Rollins
*Attorney, Agent, or Firm*—Bucknam and Archer

[57] ABSTRACT

The present invention relates to new therapeutic uses of lipophilic extracts of *Commiphora mukul*, prepared from exudate of said plant, as well as the preparation of pure compounds or highly standardized fractions thereof as active ingredients. The extracts, the fractions thereof or the single pure active ingredients isolated therefrom proved to be useful in the treatment of inflammations, both of allergic origin and not, concerning skin and external mucosae, and in the symptomatic treatment of benign prostatic hypertrophy and in the resolutive treatment of acne.

4 Claims, No Drawings

COMMIPHORA MUKUL EXTRACTS AND THERAPEUTICAL APPLICATIONS THEREOF

The present invention relates to new therapeutical applications of extracts, fractions and single active ingredients prepared from *Commiphora mukul*; the invention further relates to processes for the preparation of the total steroidal fraction which is present in the exudate of the above plant. The *Commiphora mukul* (Hook, ex Stocks) Engl. (syn. *Balsamodendron mukul* Hook) is a small tree of the Burseraceae family, endemic in the Indian peninsula, growing spontaneously in the dry and semidry Rajasthan, Gujarat and Madhya Pradesh districts in India, and in Beluchistan district in Pakistan. If the trunk is etched, the plant emits a yellowish gummy exudate, which coagulates rapidly in the form of stalactites having balsamic smell In the ancient Sanskrit, this gum resin is called guggulu and is a product which is still used in Indian popular medicine for the treatment of obesity and some arthritic forms. Recently, a lipophilic extract has been prepared from this resin, this extract containing many classes of compounds, among which lignans, terpenes and some keto-steroids, named Guggulsterones. Hypolipidemic and platelet aggregation inhibiting activities are described for this lipophilic extract, which is normally obtained by simple resin extraction with ethyl acetate, or for Guggulsterone-Z and Guggulsterone-E, whose components in the extract are normally titrated.

By studying this resin, it has surprisingly been found that the lipophilic extract with ethyl acetate or some fractions obtained from it according to the procedures described hereinbelow procedures, have a marked antiinflammatory and immunomodulating activity, over the antiandrogenic activity, useful in acne affections and in benign prostatic hypertrophy.

According to the present invention, the claimed products are prepared by etching *Commiphora mukul* bark and obtaining the resin from it. The resin is then dried, ground and subjected to exhaustive extraction with ethyl acetate. The collected extracts are treated with an amount of vegetal charcoal equivalent to 5% of the starting weight of the resin. After charcoal elimination, the colourless solution is concentrated to obtain a thick paste, which is recovered with ethanol, and, after filtrating the insoluble matter, concentrated till complete solvent removal.

For some applications, the residue from the distillation may be used whether as such, incorporated in the most common pharmaceutical compositions, or fractionated by silica or alumina gel column chromatography, or countercurrently extracted between alcohols and aliphatic hydrocarbons, or, alternatively, treated with reagents selective for the isolation of keto compounds, as in the case of Guggulsterones. In order to prepare the Guggulsterone-enriched fraction, a portion of the above described extract is suspended in 10 parts of a water-miscible aliphatic alcohol and reacted with an amount of Girard's reagent P or T ranging from 0.1 to 1 part by weight, in acidic medium (acetic acid); the reaction mixture is kept under stirring for 1 to 24 hours at a temperature ranging from 20° to 80° C., according to the alcohol used. At the end of the reaction, the alcoholic solution is diluted with the same volume of water and counterextracted with ethyl acetate. The organic phase is discarded and the aqueous phase is treated with diluted HCl at room temperature until the complete hydrolysis of the steroid/Girard's reagent adduct is achieved. The acidic solution is further subjected to countercurrent extraction with ethyl acetate or chlorinated solvents, in order to recover the fraction containing the Guggulsterones. The single components are isolated from this fraction according to well-known methods, or by means of silica gel column chromatography, optionally followed by acetylation.

The products of the present invention, when administered by the epicutaneous route, proved to have a surprisingly antiinflammatory activity, which is comparable to hydrocortisone and indomethacin, when administered by the same route.

Guggulsterone-enriched fraction activity in croton oil test, carried out according to the method described in Agents Actions, 17, 347, 1985, is hereinbelow described by way of example.

TABLE 1

Croton oil oedema inhibition in the mouse from *Commiphora mukul* total extract and Guggulsterone enriched fraction.

| Substance | Dose/µg | Oedema/mg* | % Reduction | p< |
|---|---|---|---|---|
| Controls | — | (36)* 6,9 ± 0,3 | — | — |
| Tot. extr. | 80 | (14)* 3,8 ± 0,4 | 44,9 | 0,001 |
| | 800 | (14)* 2,0 ± 0,4 | 71,9 | 0,001 |
| Guggulst.- enriched fraction | 24 | (15)* 5,1 ± 0,5 | 26,1 | 0,001 |
| | 80 | (27)* 3,0 ± 0,3 | 56,5 | 0,001 |
| | 260 | (13)* 1,5 ± 0,3 | 78,3 | 0,001 |
| | 800 | (14)* 0,6 ± 0,1 | 91,3 | 0,001 |
| Indomethacin | 60 | (14)* 2,9 ± 0,4 | 58,0 | 0,001 |

*Number of animals
*Mean ± SD

The Guggulsterone-enriched fraction, used according to the present invention, in clinical tests on dermatological affections, such as atopic dermatitis, psoriasis or inflamed states of various origin, such as U.V. radiation or radiotherapy induced erythema, produces remarkable improvements without causing dryness in the treated part. The fraction containing the Guggulsterones proved to be particularly useful in the treatment of allergic dermatitis; from this result it can be presumed that the Guggulsterones can interfere with the immune system. The enriched fraction, or, in specific cases, pure Guggulsterones (Guggulsterone-Z and Guggulsterone-E) could be employed in the treatment of torpid ulcers and bedsores, as they stimulate cycatrization, probably through macrophage activation.

The systemic administration of the products of the invention to patients affected by benign prostatic hypertrophy having a clinical picture characterized by dysuria, diurnal and nocturnal pollakiuria and urinary retention, leads to reduction of the symptomatology, without giving noteworty side effects. The therapeutically useful doses of the Guggulsterone-enriched fraction are comprised between 100 and 1000 mg/day, while the therapeutic doses of the two Guggulsterones ranges from 10 to 150 mg/day.

All these products are appropriately incorporated in the most common pharmaceutical compositions. Particularly, for the topical treatment, liposomial lipogels ensure a controlled release and reduce systemic absorption.

The following examples further illustrate the invention.

EXAMPLE 1

Preparation of the Total Extract 1 kg of dryed and finely ground *Commiphora mukul* resin was extracted under stirring with 10 l of ethyl acetate first at room temperature, then under mild reflux; after filtering the insoluble matter, the residue was extracted with further 10 l of the same solvent under the same conditions. The collected extracts were treated with 0.05 kg of ENO vegetal charcoal and, after 3 hours under mild reflux, filtered. The bright-yellow clear solution was vacuum-concentrated at 40° C. to the pasty form (very thick honey) and the residue was diluted with 5 l of ethanol. The ethanolic solution was filtered and vacuum concentrated. 0.42 kg of an amber-coloured semifluid material containing about 20% of total Guggulsterones were obtained.

EXAMPLE 2

Preparation of the Total Steroidal Fraction 50 g of the extract prepared according to the procedure of Example 1 were suspended in 500 ml of ethanol and added to 50 g of Girard's T reagent, together with 50 ml of glacial acetic acid. The solution was heated to mild reflux for 90 minutes.

At the end of the reaction, the alcoholic solution was diluted with about 1 l of ethyl acetate and counterwashed three times with 2.5 l of water. The aqueous phase was added to 250 ml of concentrated HCl and kept at 60° C. for one hour.

After the acidic hydrolysis, the turbid aqueous solution was extracted three times with 500 ml each of ethyl acetate until complete exhaustion of the steroidal compounds. After drying the etheroacetic phase over $Na_2SO_4$ and concentrating to dryness, 10.5 g of a product almost completely consisting of Guggulsterones and Guggulsterols were obtained.

EXAMPLE 3

Preparation of Pure Guggulsterones 10 g of the fraction obtained according to Example 2 were dissolved in a 8:2 cyclohexane/acetone mixture and chromatographed on a 200 g silica gel column. Guggulsterone-E could be isolated using the above mixture as eluent. Guggulsterone-Z was instead obtained together with Guggulsterol, which could subsequently be separated by acetylating and crystallizing from an aqueous alcohol.

We claim:

1. A process for the preparation of the total steroidal fraction from the resin of *Commiphora mukul* bark, which comprises the following steps:
   1) etching the *Commiphora mukul* bark whereby an exudate is obtained in the form of a gummy resin;
   2) extracting exhaustively said resin with ethyl acetate whereby an extract is obtained;
   3) treating with vegetal charcoal said extract from step 2); filtering said charcoal and concentrating said extract to obtain a thick paste;
   4) diluting the thick paste from step 3) with ethanol, filtering off the insoluble matter and distilling off the solvent, whereby a semifluid material containing 20% of total Guggulsterone is obtained;
   5) suspending said semifluid material from step 4) in a water-ethanol mixture and reacting the suspension with a reagent capable of reacting selectively with a keto compound to form an adduct and making the reaction mixture acidic with acetic acid;
   6) diluting the reaction mixture from step 5) with water and counterextracting with ethyl acetate to obtain an aqueous phase and an ethyl acetate phase;
   7) disregarding the ethyl acetate phase from step 6), acidifying the aqueous phase with dilute HCl in order to hydrolyze said adduct whereby a torbid aqueous solution is obtained;
   8) extracting the torbid solution from step 7) countercurrently using ethyl acetate or a chlorinated solvent to obtain an ethyl acetate or a chlorinated solvent extract;
   9) drying said extract from step 8) and concentrating to dryness said dried extract to obtain a product consisting essentially of Guggulsterones and Guggulsterols.

2. The process of preparation of pure Guggulsterone-E and Guggulsterone-Z from the resin of *Commiphora mukul* bark, which comprises the following steps:
   1) etching the *Commiphora mukul* bark whereby an exudate is obtained in the form of a gummy resin;
   2) extracting exhaustively said resin with ethyl acetate whereby an extract is obtained;
   3) treating with vegetal charcoal said extract from step 2), filtering said charcoal and concentrating said extract to obtain a thick paste;
   4) diluting the thick paste from step 3) with ethanol, filtering off the insoluble matter and distilling off the solvent whereby a semifluid materials containing 20% of total Guggulsterone is obtained;
   5) suspending said semifluid material from step 4) in a water-ethanol mixture and reacting the suspension with a reagent capable of reacting selectively with a keto compound to form an adduct and making the reaction mixture acidic with acetic acid;
   6) diluting the reaction mixture from step 5) with water and counterextracting with ethyl acetate to obtain an aqueous phase and an ethyl acetate phase;
   7) disregarding the ethyl acetate phase from step 6), acidifying the aqueous phase with dilute HCl in order to hydrolyze said adduct whereby a torbid aqueous solution is obtained;
   8) extracting the torbid solution from step 7) countercurrently using ethyl acetate or a chlorinated solvent to obtain an ethyl acetate or a chlorinated solvent extract;
   9) drying said extract and concentrating to dryness said dried extract to obtain a product consisting essentially of Guggulsterones and Guggulsterols;
   10) dissolving said product from 9) in a mixture of cyclohexanone and acetone to obtain a solution, subjecting said solution to chromatography on a silica gel column, eluting with a mixture of cyclohexanone and acetone whereby said Guggulsterone-E is first eluted and then recovering Guggulsterone-Z together with Guggulsterol.

3. The method of treatment of a patient affected by benign prostatic hypertrophy with symptoms of dysuria, diurnal and nocturnal pollakiuria and urinary retention, which consists of administering topically to said patient a composition containing as the active ingredient 100-1000 mg/day of the Guggulsterone enriched fraction obtained from the resin of *Commiphora mukul* bark by
   1) etching the *Commiphora mukul* bark whereby an exudate is obtained in the form of a gummy resin;

2) extracting exhaustively said resin with ethyl acetate whereby an extract is obtained;
3) treating with vegetal charcoal said extract from step 2), filtering said charcoal and concentrating said extract to obtain a thick paste;
4) diluting the thick paste from step 3) with ethanol, filtering off the insoluble matter and distilling off the solvent whereby a semifluid material containing 205 of total Guggulsterone is obtained;
5) suspending said semifluid material from step 4) in a water-ethanol mixture and reacting the suspension with a reagent capable of reacting selectively with a keto compound to form an adduct and making the reaction mixture acidic with acetic acid;
6) diluting the reaction mixture from step 5) with water and counterextracting with ethyl acetate to obtain an aqueous phase and an ethyl acetate phase;
7) disregarding the ethyl acetate phase from step 6), acidifying the aqueous phase with dilute HCl in order to hydrolyze said adduct whereby a torbid aqueous solution is obtained;
8) extracting the torbid solution from step 7) countercurrently using ethyl acetate or a chlorinated solvent to obtain an ethyl acetate of a chlorinated solvent extract;
9) drying said extract and concentrating to dryness said dried extract to obtain a product consisting essentially of Guggulsterones and Guggulsterols.

4. The method of treatment of a patient affected by allergic dermatitis, psoriasis, inflammation due U.V. radiation or radiotherapy induced erythema which consists of topically administering to said patient a composition containing as the active ingredient the Guggulsterone-enriched fraction obtained from the resin of *Commiphora mukul* bark by the following steps
1) etching the *Commiphora mukul* bark whereby an exudate is obtained in the form of a gummy resin;
2) extracting exhaustively said resin with ethyl acetate whereby an extract is obtained;
3) treating with vegetal charcoal said extract from step 2), filtering said charcoal and concentrating said extract to obtain a thick paste;
4) diluting the thick paste from step 3) with ethanol, filtering off the insoluble matter and distilling off the solvent, whereby a semifluid material containing 20% of total Guggulsterone is obtained;
5) suspending said semifluid material from step 4) in a water-ethanol mixture and reacting the suspension with a reagent capable of reacting selectively with a keto compound to form an adduct and making the reaction mixture acidic with acetic acid;
6) diluting the reaction mixture from step 5) with water and counterextracting with ethyl acetate to obtain an aqueous phase and an ethyl acetate phase;
7) disregarding the ethyl acetate phase from step 6), acidifying the aqueous phase with dilute HCl in order to hydrolyze said adduct whereby a torbid aqueous solution is obtained;
8) extracting the torbid solution from step 7) countercurrently using ethyl acetate or a chlorinated solvent to obtain an ethyl acetate or a chlorinated solvent extract;
9) drying said extract and concentrating to dryness said dried extract to obtain a product consisting essentially of Guggulsterones and Guggulsterols.

* * * * *

UNITED STATES PATENT AND TRADEMARK OFFICE
CERTIFICATE OF CORRECTION

PATENT NO. : 5,273,747

DATED : December 28, 1993

INVENTOR(S) : Ezio Bombardelli, et al

It is certified that error appears in the above-identified patent and that said Letters Patent is hereby corrected as shown below:

Column 4,

Claim 3, line 4, delete "topically" and substitute therefor: -- systemically --.

Signed and Sealed this

Eleventh Day of February, 1997

Attest:

BRUCE LEHMAN

Attesting Officer     Commissioner of Patents and Trademarks